United States Patent
Ash et al.

(10) Patent No.: US 9,110,553 B2
(45) Date of Patent: Aug. 18, 2015

(54) HEALTH FORECASTER

(75) Inventors: Michael A. Ash, Parkville, MO (US); Todd Jeffrey Reynolds, Kansas City, MO (US); Harlen Hays, Lawrence, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

(21) Appl. No.: 13/399,278

(22) Filed: Feb. 17, 2012

(65) Prior Publication Data
US 2013/0174073 A1 Jul. 4, 2013

Related U.S. Application Data

(60) Provisional application No. 61/580,945, filed on Dec. 28, 2011.

(51) Int. Cl.
*G06F 3/048* (2013.01)
*G06Q 40/08* (2012.01)

(52) U.S. Cl.
CPC ............. *G06F 3/048* (2013.01); *G06Q 40/08* (2013.01)

(58) Field of Classification Search
CPC ..... G06F 19/322; G06F 3/04847; G06F 8/34; G06F 3/0481; A61B 5/4872; A61B 5/744; Y10S 128/92
USPC .................................................. 715/771, 706
See application file for complete search history.

(56) References Cited

U.S. PATENT DOCUMENTS

| | | | | |
|---|---|---|---|---|
| 5,673,691 | A * | 10/1997 | Abrams et al. | 600/300 |
| 2002/0156654 | A1* | 10/2002 | Roe et al. | 705/3 |
| 2004/0002634 | A1* | 1/2004 | Nihtila | 600/300 |
| 2005/0113650 | A1* | 5/2005 | Pacione et al. | 600/300 |
| 2005/0283387 | A1* | 12/2005 | Donoghue et al. | 705/3 |
| 2006/0089543 | A1* | 4/2006 | Kim et al. | 600/300 |
| 2009/0204439 | A1* | 8/2009 | Turton | 705/3 |
| 2010/0249531 | A1* | 9/2010 | Hanlon et al. | 600/300 |
| 2012/0127157 | A1* | 5/2012 | Adler et al. | 345/419 |

OTHER PUBLICATIONS

"Wii Fit", May 21, 2008, Nintendo, [retrieved on: Jun. 6, 2013], Retrieved from the Internet: <URL: http://www.nintendo.com/games/detail/hoiNtus4JvlcPtP8LQPyud4Kyy39​3oep/>, p. 1-2.*
Brad McCarty, "Lose weight and stay healthy with Usable Health", Oct. 27, 2010, [retrieved on Jun. 6, 2013], Retrieved from the Internet: <URL: http://thenextweb.com/apps/2010/10/27/usable-health-make-better-food-choices-lose-weight-stay-healthy/>, p. 1-2.*

(Continued)

*Primary Examiner* — Omar Abdul-Ali
*Assistant Examiner* — Mong-Shune Chung
(74) *Attorney, Agent, or Firm* — Shook, Hardy & Bacon L.L.P.

(57) ABSTRACT

Methods, computer systems, and computer-readable storage media are provided for utilizing health-related variables to generate a current health state of a user along with a most-likely future health state of the user and an ideal future health state of the user. Graphical representations of these health states are generated and presented on a graphical user interface. The user is able to interact with the graphical representations to see the impact of the user's choices on the user's future health.

5 Claims, 10 Drawing Sheets

(56) References Cited

OTHER PUBLICATIONS

Knowledge Base of Health, "Calculator Body Fat Index", [retrieved on Jun. 10, 2013], Retrieved from the Internet: <URL: http://articles-health.info/calculator-body-fat-index.html/>, p. 1-3.*

Credo Reference, "principal component analysis", [retrieved on Jun. 7, 2013], Retrieved from the Internet: <URL: http://www.credoreference.com/entry/penguinmath/principal_component_analysis/>, p. 1.*

"Mii", Mar. 4, 2010, Wikipedia, [retrieved on: Nov. 27, 2013], Retrieved from the Internet: <URL: http://web.archive.org/web/20100304015742/http://en.wikipedia.org/wiki/Mii/>, p. 1-4.*

Bart G. Farkas, "Mii and You", Apr. 23, 2007, [retrieved on Nov. 27, 2013], Retrieved from the Internet: <URL: http://www.peachpit.com/articles/article.aspx?p=728645&seqNum=2/>, p. 1-5.*

* cited by examiner ial Application No. 61/580,945, filed Dec. 28, 2011, entitled "Health Forecaster." The entirety of the aforementioned application is incorporated by reference herein.

HEALTH FORECASTER

CROSS-REFERENCE TO RELATED APPLICATIONS

This application, claims the benefit of U.S. Provisional Application No. 61/580,945, filed Dec. 28, 2011, entitled "Health Forecaster." The entirety of the aforementioned application is incorporated by reference herein.

BACKGROUND

With the complexity and volume of health-related information in today's modern world, healthcare consumers, and even clinicians, often struggle with comprehending how this information influences a person's health. A lab result indicating that a person's ApoB level is elevated has little effect on the typical healthcare consumer because it lacks any type of visceral, personal impact. As well, healthcare consumers often have little idea how their current lifestyle decisions or health conditions will impact their lives, both physically and mentally, in the future.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief, and at a high level, the present invention is directed to a health forecaster. The health forecaster is an interactive tool targeted to healthcare consumers and clinicians. The health forecaster utilizes health-related variables to generate a current health state of a user as well as a projected future health state of the user. The health states are graphically represented on an interactive graphical user interface along with goals and recommendations to help the user achieve an ideal future health state. The graphical user interface is designed to engage the user in a way that traditional healthcare information fails to do and to provide encouragement to the user to make needed changes to ensure a healthier future.

Aspects of the present invention are directed to one or more computer-readable storage media, executable by a computing device, to display a graphical user interface (GUI) for displaying a current health state of a user and one or more projected future health states of the user. The GUI comprises a first display area configured to display one or more graphical representations of health-related variables associated with the user at a current period of time as well as a second display area configured to display one or more graphical representations of health-related variables associated with the user at a future period of time. Additionally, the GUI comprises a third display area configured to display goals and recommendations related to the user achieving an ideal future health state.

In another aspect, the present invention is directed to one or more computer-readable storage media, executable by a computing device, to display a graphical user interface (GUI) for displaying graphical representations of a current and future health state of a user along with goals and recommendations for achieving an ideal future health state. The GUI includes a body-image representation of a user; the body-image representation comprises a graphical representation of health-related variables associated with the user at a current or future period of time. The GUI also comprises a first display area configured to display one or more selectable user-customized goals to enable the user to achieve an ideal future health state. Incident to the user selecting at least one of the user-customized goals, a second display area is configured to display a selectable set of recommendations to enable the user to achieve the at least one user-customized goal. Incident to the user selecting at least one recommendation, a third display area is configured to display a graphical representation of the at least one user-customized goal over a future period of time.

In yet another aspect, the present invention is directed to one or more computer-readable storage media having embodied thereon computer-executable instructions that, when executed by a server, perform a method of using health-related variables associated with a user having a health condition to generate current and future health states of the user. The method comprises receiving structured and unstructured health-related data associated with the user; the health-related data comprises data over a past period of time up to a current period of time and also comprises general data about the user and specific data about the health condition. The structured and unstructured data are codified to form a set of codified concepts of standard nomenclature. The codified concepts are used to determine a current health state of the user where the current health state comprises a percentile comparison of the user to members of the population-at-large. As well, the codified concepts are used determine a most-likely future health state of the user based on the general data about the user and the specific data about the health condition.

Continuing, a first graphical representation of the current health state of the user is generated, and a second graphical representation of the most-likely future health state of the user is generated. The first and second graphical representations are rendered on a graphical user interface.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, computer systems, and computer-readable storage media for generating and displaying health-related information associated with a user. Past and current health-related information associated with the user are used to generate and present graphical representations corresponding to a current health state of the user as well as a likely future health state of the user. The user is able to select from a variety of customized goals to help the user achieve an ideal future health state. In response to the selected goals, recommendations are generated and presented to the user. The user is able to select recommendations that the user is likely to follow, and the user can visualize his or her health state over a period of years based on the selected recommendations. The above-described health forecaster is an easy-to-use interactive tool that educates healthcare consumers about the impact their choices have on lifestyle, health, and physical appearance.

Figure 1:
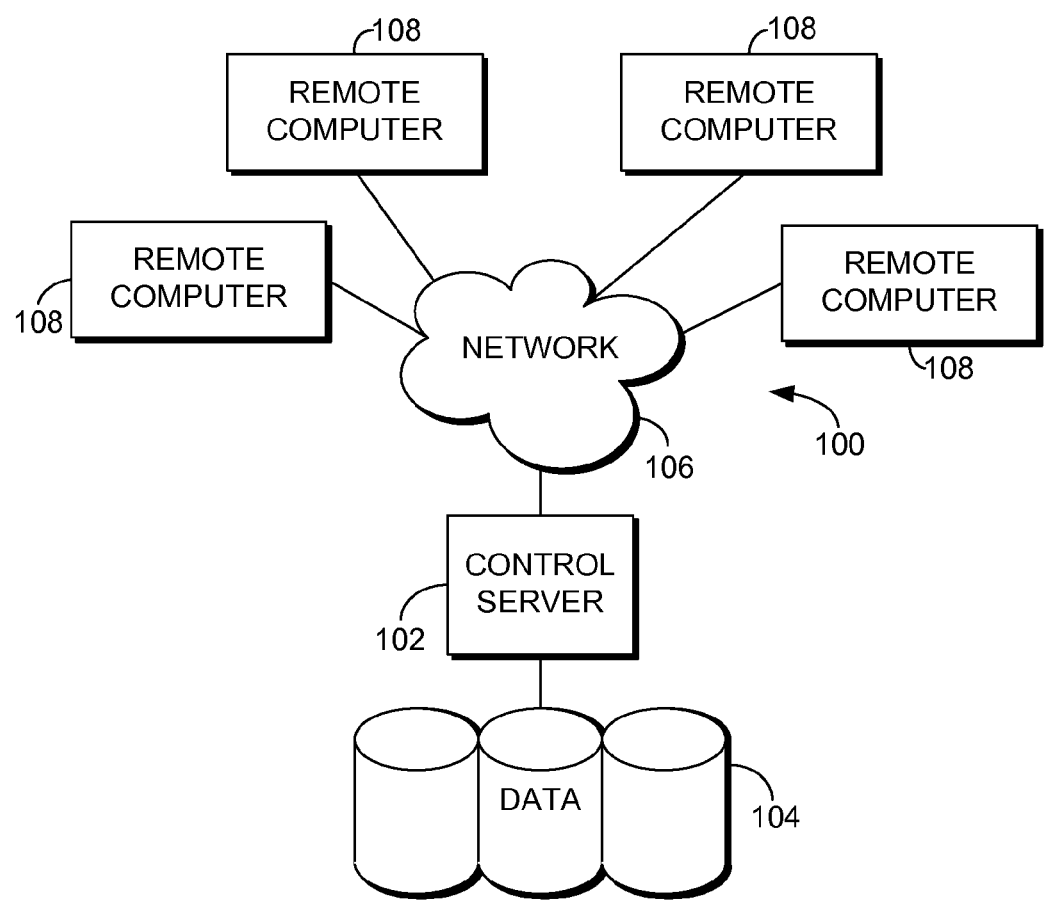
FIG. 1 is a block diagram of an exemplary computing environment suitable to implement embodiments of the present invention.

Having provided a high-level overview of the present invention, an exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
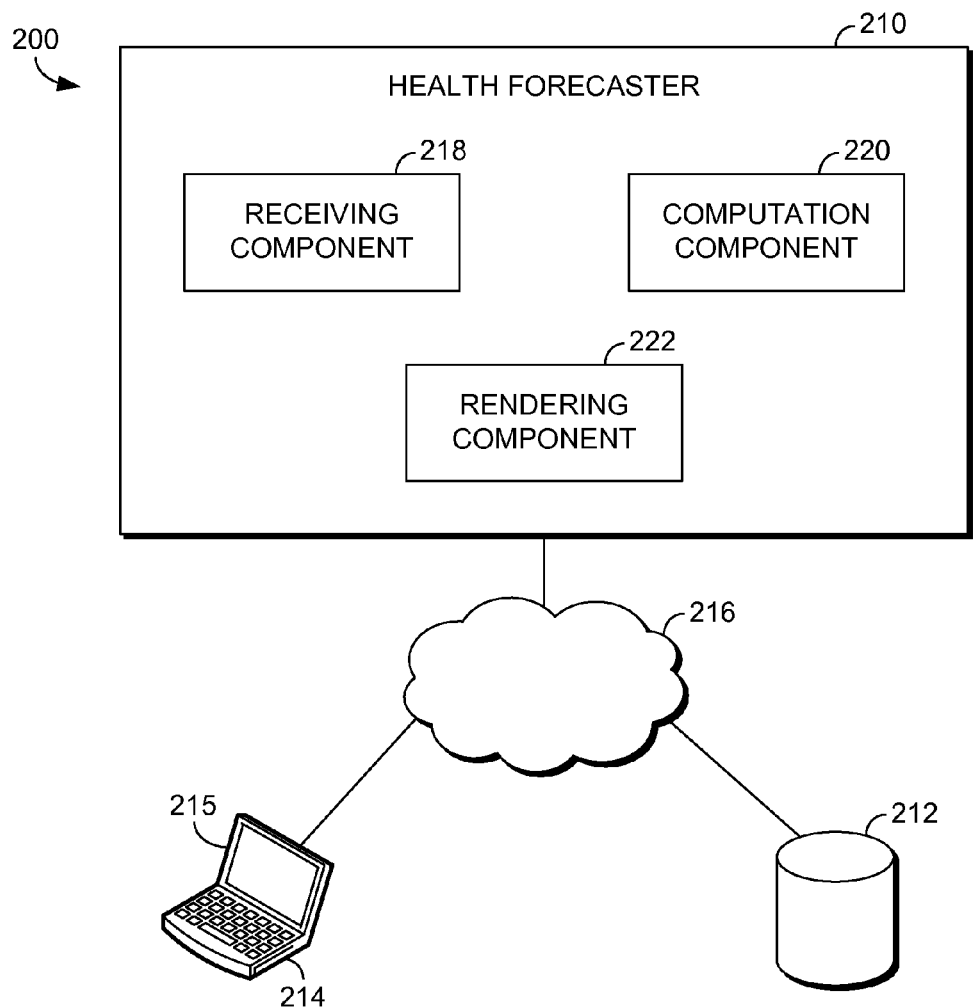
FIG. 2 is a block diagram of an exemplary computing system environment suitable for generating current and future health states of a user and graphical representations of the current and future health states suitable to implement embodiments of the present invention.

Turning now to FIG. 2, an exemplary computing system environment 200 is depicted. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes a health forecaster 210, a data store 212, and an end-user computing device 214 with a display screen 215 all in communication with one another via a network 216. The network 216 may include, without limitation, one or more local area networks (LANs) and/or wide area networks (WANs). Such networking environments are commonplace in offices, enterprise-wide computer networks, intranets and the Internet. Accordingly, the network 216 is not further described herein.

In some embodiments, one or more of the illustrated components/modules may be implemented as stand-alone applications. In other embodiments, one or more of the illustrated components/modules may be integrated directly into the operating system of the health forecaster 210. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the health forecaster 210 might reside on a server, cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The data store 212 is configured to store information for use by, for example, the health forecaster 210. The information stored in association with the data store 212 is configured to be searchable for one or more of the items of information stored in association therewith. The information stored in association with the data store 212 may comprise general information about health-related variables used by the health forecaster 210. As used throughout this application, the term "health-related variables" means any piece of health-related information. This may include everything from patient identifying information, to decision support algorithms, to a specific lab value. As such, it is meant to be a broad definition that encompasses the many pieces of information used in healthcare and related to a person's health. Health-related information may take the form of personal health risk assessments, biometric screenings, health-related insurance claims, information stored in association with an electronic medical record, and the like. Further, this information or data may be structured or unstructured.

A personal health risk assessment is a questionnaire that gathers information concerning the user's health history (both physical and mental) and lifestyle; it is generally completed by the user or the user's representative. Biometric screenings are screening tests and procedures designed to capture general health information. Information from biometric screenings may include information related to height, weight, blood pressure, as well as general lab results that measure glucose levels, cholesterol levels, thyroid levels, and the like. Health-related insurance claims provide information such as diagnosed conditions, number of hospital visits including emergency room visits, reasons for visits, costs associated with care, and the like.

The EMR may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

As well, the data store 212 may store information concerning decision-support algorithms, reference materials, recommendation protocols, and the like. This information may be used by the health forecaster 210 to determine, for example, alternative recommendations if a user is unwilling or unable to follow a prescribed recommendation to achieve an ideal future health state. The data store 212 may also store health-related information associated with the population-at-large including health-related information associated with a particular demographic group (gender, race, geographic distribution, etc.).

The content and volume of such information in the data store 212 are not intended to limit the scope of embodiments of the present invention in any way. Further, though illustrated as a single, independent component, the data store 212 may, in fact, be a plurality of storage devices, for instance, a database cluster, portions of which may reside on the health forecaster 210, the end-user computing device 214, and/or any combination thereof.

As shown, the end-user computing device 214 includes a display screen 215. The display screen 215 is configured to display information to the user of the end-user computing device 214, for instance, information relevant to communications initiated by and/or received by the end-user computing device 214, information concerning graphical representations of health-related variables, and/or the like. Embodiments are not intended to be limited to visual display but rather may also include audio presentation, combined audio/visual presentation, and the like. The end-user computing device 214 may be any type of display device suitable for presenting a graphical user interface. Such computing devices may include, without limitation, a computer, such as, for example, any of the remote computers 108 described above with reference to FIG. 1. Other types of display devices may include tablet PCs, PDAs, mobile phones, smart phones, as well as conventional display devices such as televisions.

Components of the health forecaster 210 may include a processing unit, internal system memory, and a suitable system bus for coupling various system components, including one or more data stores for storing information (e.g., files and metadata associated therewith). The health forecaster 210 typically includes, or has access to, a variety of computer-readable media.

The computing system environment 200 is merely exemplary. While the health forecaster 210 is illustrated as a single unit, it will be appreciated that the health forecaster 210 is scalable. For example, the health forecaster 210 may in actuality include a plurality of computing devices in communication with one another. Moreover, the data store 212, or portions thereof, may be included within, for instance, the health forecaster 210 as a computer-storage medium. The single unit depictions are meant for clarity, not to limit the scope of embodiments in any form.

As shown in FIG. 2, the health forecaster 210 comprises a receiving component 218, a computation component 220, and a rendering component 222. In some embodiments, one or more of the components 218, 220, and 222 may be implemented as stand-alone applications. In other embodiments, one or more of the components 218, 220, and 222 may be integrated directly into the operating system of a computing device such as the remote computer 108 of FIG. 1. It will be understood that the components 218, 220, and 222 illustrated in FIG. 2 are exemplary in nature and in number and should not be construed as limiting. Any number of components may be employed to achieve the desired functionality within the scope of embodiments hereof.

The receiving component 218 is configured to receive health-related information stored in association with the data store 212 as well as user inputs, requests, and/or selections. For the purposes of this application, a user may be defined as any person, party, or entity interested in viewing healthcare information in a graphical form. Thus, the user may be, for instance, a patient under the care of a clinician or a general healthcare consumer. As well, the user may be a clinician who cares for any number of patients. The receiving component 218 receives requests for graphical representations of health-related variables. As well, the receiving component 218 receives user selections. The user selections may be selections of goals and recommendations, selections associated with the graphical representations of health-related variables, selections of customization variables, and the like. This process will be explained in greater depth below. Further, the receiving component 218 is configured to receive user inputs of health-related information in the form of, for example, numerical inputs, audio inputs, and/or textual inputs. For example, a user may input a weight, or possibly a blood glucose level if the user is a diabetic. As well, a clinician caring for a patient may input results from biometric screening tests, or results and/or notes from a recent clinical encounter with the patient.

As mentioned, the receiving component 218 is configured to receive health-related information stored in association with the data store 212. The health-related information is associated with a user and includes current health-related information as well as past health-related information. The health-related information may be in a structured form (e.g., ICD-9-CM or ICD-10-CM codes used on insurance claims) or an unstructured form (e.g., a clinician note). The receiving component is further configured to codify the structured and unstructured health-related information into a set of discrete concepts of standard nomenclature. Exemplary standard nomenclatures may include the Systemized Nomenclature of Medicine (SNOMED), and/or Logical Observation Identifiers Names and Codes (LOINC).

The computation component 220 is configured to generate one or more current and future health states associated with the user. A health state is a mathematical expression of the user's current and future health and is based on health-related information associated with the user. A user's health state can be represented by an overall health score as well as health scores related to discrete subcomponents of health. Examples of subcomponents of health may include cardiovascular health, mental health, acute health, chronic disease health, physical fitness health, weight health, and the like.

In one aspect, the computation component 220 utilizes principal component analysis (PCA) to reduce the set of discrete concepts of standard nomenclature to a finite set of health scores that represents the user's current and/or future health state. A health score is a percentile score bounded between 0 and 100 and gives an indication of the user's overall health or the user's health with respect to one or more discrete health-related variables as compared to members of the population-at-large or subsets of the population-at-large. In general, PCA is a statistical technique that generates a finite set of factors from an initial set of correlated variables (in this case, the initial set of correlated variables is part of the set of discrete concepts of standard nomenclature). The initial set of correlated variables may comprise health-related variables drawn from personal health risk assessments, biometric screenings, health-related insurance claims, an electronic medical record, inputted values, and the like. Each factor is a rotated linear weighted combination of the initial set of correlated variables. With respect to the present application, the factors have been rotated via the oblique varimax methodology allowing for one variable to load on multiple factors.

Figure 3:
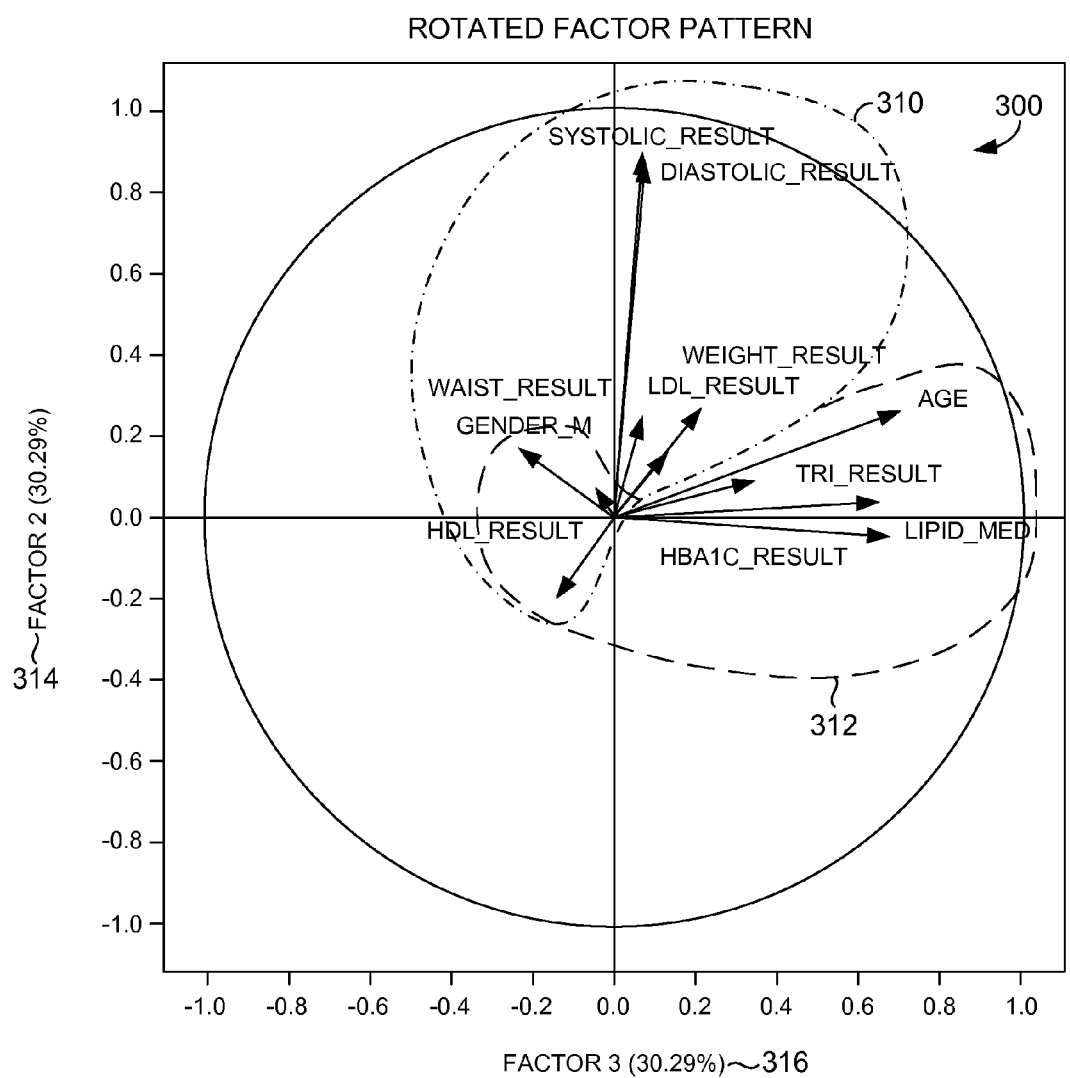
FIG. 3 depicts an exemplary rotated factor pattern used to classify health-related variables into different factors in accordance with an embodiment of the present invention.

FIG. 3 is an exemplary rotated factor pattern 300. The rotated factor pattern 300 comprises a first set of correlated variables 310 that load on Factor 2 (element 314). The first set of correlated variables 310 includes, for example, such variables as blood pressure, gender, waist circumference, weight, LDL, and HDL. Thus, Factor 2 could generally be described as cardiovascular health. Because these variables are correlated, an increase in, for example, weight may cause an increase in LDL and a decrease in HDL. Thus, variables that load on any particular factor may be positively correlated with each other (i.e., an increase in weight leads to an increase in LDL) or negatively correlated with each other (i.e., an increase in weight leads to a decrease in HDL).

The rotated factor pattern 300 also comprises a second set of correlated variables 312 that load on Factor 3 (element 316). The second set of correlated variables 312 includes age, triglycerides, lipid medication, HbA1c (glycated hemoglobin), HDL, gender, and waist circumference. Thus, Factor 3 could generally be described as medication compliance health. As can be seen, user compliance in taking lipid medication is correlated with, for example, alterations in triglyceride levels, HDL levels, and HbA1c levels. As mentioned above, a variable may load on more than one factor. The rotated factor pattern 300 illustrates that gender, for example, loads on both Factor 2 and Factor 3.

The number of factors derived from the initial set of correlated variables may be restricted in number such that only meaningful amounts of variance are accounted for. In one aspect, each factor may encompass a different number of variables, with the number of variables associated with any one factor being dependent upon the degree of correlation between the variables—highly-correlated variables are likely to be associated with the same factor. In another aspect, each factor may encompass the same number of variables, but a variable may be weighted differently within each factor. Factors may encompass variables related to, for example, overall health, cardiovascular health, medication compliance health, mental health, acute health, injury risk, chronic disease risk, and the like.

Next, the computation component 220 generates a health score for each factor that indicates where the user stands with respect to that factor. Again, this is accomplished using PCA. The health score (otherwise known as a factor score or component score in PCA) is a linear composite of the optimally-weighted health-related variables. A health score may be generated for each one of the retained factors by converting the Z-score created by each factor calculation into a percentile rank. The Z-score follows a normal distribution with a mean equal to zero. This is accomplished through look-up table conversions of the Z-score. Thus, each score can be interpreted as measuring a different facet of health such as an overall health score, a mental health score, an acute health score, an injury risk health score, a chronic disease risk health score, and the like. Again, each variable (e.g., body mass index) can contribute to multiple different health scores.

Figure 4:
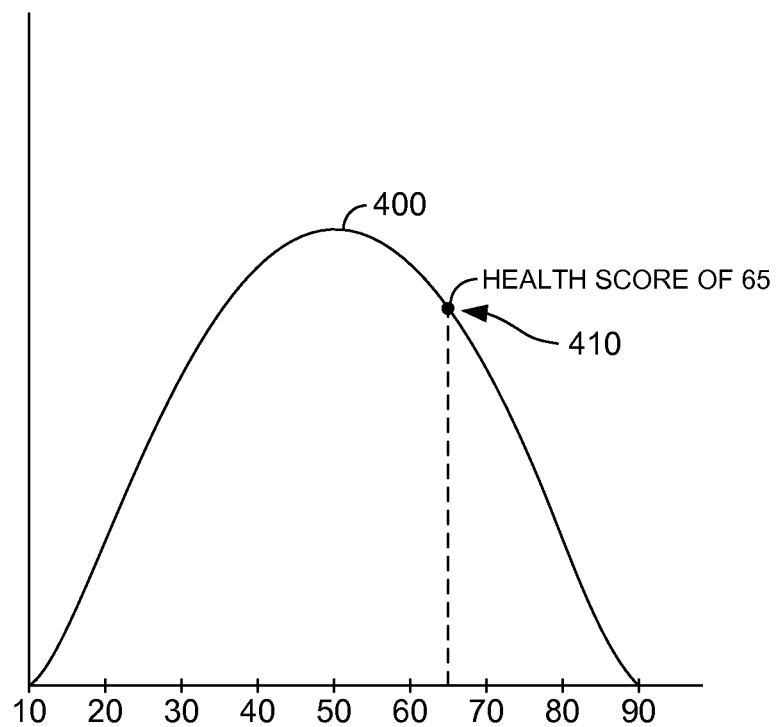
FIG. 4 depicts an exemplary bell-shaped curve and a generated health score in accordance with an embodiment of the present invention.

As mentioned above, a health score is a percentile bounded between 0 and 100 and gives an indication of where the user stands with respect to any one factor as compared to members of the population-at-large. This is graphically shown in FIG. 4 which depicts a bell-shaped curve 400 with a Gaussian distribution corresponding to a particular factor (for example, a mental health factor). Utilizing the Z-score calculated for the factor deemed to represent mental health, a Z-score of approximately 0.35 would be converted to an overall mental health score of 65 for a user (shown at element 410), indicating that the user has a mental health score that is better than 65% of the population.

When the user is compared to a subset of the population-at-large, further calibration is needed to give an accurate portrayal of the user's health status in relation to others within the subset. For example, the same Z-score calculated for mental health can also be used to create a percentile rank limited to one gender. This further step requires calibrating the percentile rank to be among only individuals of one gender. This is done by creating a normal distribution of the Z-score among the gender of interest and then converting the new position within the bell curve to a percentile rank. Thus, it is possible for an individual to have a mental health score in the $65^{th}$ percentile when compared to the population-at-large but to have a mental health score in the $80^{th}$ percentile when compared to individuals who are the same gender as the user.

The computation component 220 is also configured to determine a current health trajectory leading to a most-likely future health state based upon the user's past and current health-related variables. Using known regression techniques such as, for example, proportional hazard models, CART regression, and/or logistic regression, the computation component 220 determines how likely the user is to have a particular health state at a given point in time in the future based upon current characteristics or behaviors. From these probabilities a significantly large number of future health state scenarios can be calculated for the user based upon a nearly infinite number of possible future decisions.

In order to identify the most likely path that will be followed by the user, optimal stopping theory is applied. Stopping rules are identified for the different input parameters to create appropriate thresholds that should be met before the algorithm will stop computing. The purpose is to maximize a match to one of the nearly infinite number of potential future health states while minimizing the computing and processing time.

By way of illustrative example, a 33-year-old user has a number of biometric readings (triglycerides, LDL, HDL, and body mass index (BMI)), and a personal health assessment indicative of a sedentary lifestyle. Further, the user's biometric readings over the past couple of years show a slowly increasing LDL and BMI. Using the principles of PCA outlined above, the user is initially identified as being in the $50^{th}$ percentile of overall health as compared to the population-at-large. Using regression analysis and applying optimal stopping to the biometric readings identified above, a most-likely future health state of the user is generated. The most-likely future health state demonstrates that the user will be in the $25^{th}$ percentile of overall health (as determined through PCA) and will have a significantly increased risk of cardiovascular disease. As can be seen, if the user continues his current behaviors, his health state as compared to others will gradually decline through the years.

The computation component 220 is furthered configured to generate goals related to the user achieving an ideal future health state. In one aspect, the user may indicate that he or she would like to have an overall health score in the 90$^{th}$ percentile in the future. Utilizing this information as well as information concerning the user's past and current characteristics, goals directed toward helping the user reach the 90$^{th}$ percentile are generated. In another aspect, the user can input values related to individual health-related variables, and the computation component 220 determines goals designed to help the user reach these values. Using the example given above, the 33-year-old user has a current BMI of 28. The user inputs a future BMI value of 24, and the computation component 220 determines that this would place the user in the 70$^{th}$ percentile of healthcare consumers; goals would then be determined that would help the user achieve the future BMI value of 24 (and, by extension, help the user to achieve a 70$^{th}$ percentile ranking for BMI).

Next, the user indicates which goals the user is willing or able to follow. Decision support algorithms (stored in association with, for example, the data store 212) may be used to generate alternative goals if the user is not willing or is unable to follow a goal. For instance, a goal to decrease percent body fat may be to lose weight. However, the user is happy with his or her weight and does not select that goal. Decision support algorithms may determine that increasing exercise would also help the user to achieve the goal of decreasing percent body fat without losing weight.

Once the user indicates what goals the user is willing or is able to follow, the computation component 220 generates recommendations related to the user achieving the selected goals. The recommendations may be customized to the user, customized based on demographic characteristics associated with the user, or may be general recommendations designed for any healthcare consumer. For example, a selected goal may be to lose weight, and previous testing indicates that the user metabolizes food differently from others and would effectively lose weight using a combination of a reduced carbohydrate diet and exercising at small intervals on a daily basis. Thus, recommendations to help the user achieve his or her goal of losing weight would be customized based on the above information. In another example, recommendations may be customized based on demographic features associated with the user. For instance, recommendations regarding weight loss may differ based on gender, what geographic region the user resides, race, and the like.

Decision support algorithms may also be utilized when generating recommendations. For example, a recommendation may be to take a certain medication on a daily basis to help improve cardiovascular health. The user may be unwilling or unable to follow this recommendation because of side effects associated with the medication. Decision support algorithms are used to generate alternative recommendations such as, for example, following a reduced-fat diet instead of taking the medication.

The computation component 220 is configured to utilize PCA to determine health scores associated with the ideal future health state. Further, the computation component 220 is configured to update the models described above (current health state, most-likely future health state, and ideal future health state) as new health-related variables are received. Updated models may be generated at predetermined intervals (i.e., once every six months, once a year, etc.). Alternatively, updated models may be generated every time a user inputs a new variable. Any and all such aspects are within the scope of the invention.

Next, the rendering component 222 is configured to render for display one or more graphical representations of the models generated by the computation component 220. Thus, the graphical representations may correspond to a current health state of the user, a most-likely future health state of the user, and an ideal future health state of the user. The graphical representations may be in the form of score cards, gauges, graphs, tables, timelines, icons, pictorial representations, textual, audio, and/or numerical elements, and any combination of the above. These graphical representations will be explained in greater depth below with respect to FIGS. 6-10.

In one aspect of the invention, the graphical representation of the models may be in the form of a body-image representation. The body-image representation may be an outline of a generally male-looking body or a generally female-looking body in various different poses. The body-image representation may also be an anatomically correct, iconic representation of the user. With respect to this aspect, the user is able to customize the visual appearance of the body-image representation by selecting one or more characteristics (the selections are received by, for example, the receiving component 218). The selected characteristics may include gender, a body habitus, race, facial characteristics, hair color, and the like. The user may also be able to customize the face of the iconic representation using a picture of the user. The body-image representation may be one-dimensional or three-dimensional in nature. For example, the body-image representation may comprise a three-dimensional figure that rotates to show the front and back of the structure.

The body-image representation may, in one aspect, be outlined with a color to indicate a health problem that affects multiple organs and/or systems. Distinct disease conditions may be color-coded with distinct colors. For example, a teal outline may represent the disease condition of diabetes mellitus. Instead of outlining the body-image representation with a colored line, a colored halo may be used instead.

The rendering component 222 is also configured to render visual indicators on the body-image representation that represent areas of concern for the user. The visual indicators may be displayed over an anatomical position that corresponds to an affected organ or system. The visual indicators may be in the form of a dot, a stylized version of the affected organ and/or system, or an anatomically correct representation of the affected organ and/or system. Further, the visual indicators may be color-coded or shaped differently to indicate a status of the affected organ and/or system. By way of illustrative example, and not by limitation, the visual indicators may be color-coded red to indicate "critical," dark grey for "currently managing," orange for "needs attention," and light grey for "at risk." In another example, a solid dot may indicate "critical," a shaded dot may indicate "needs attention," and an open dot may indicate "stable."

Figure 5:
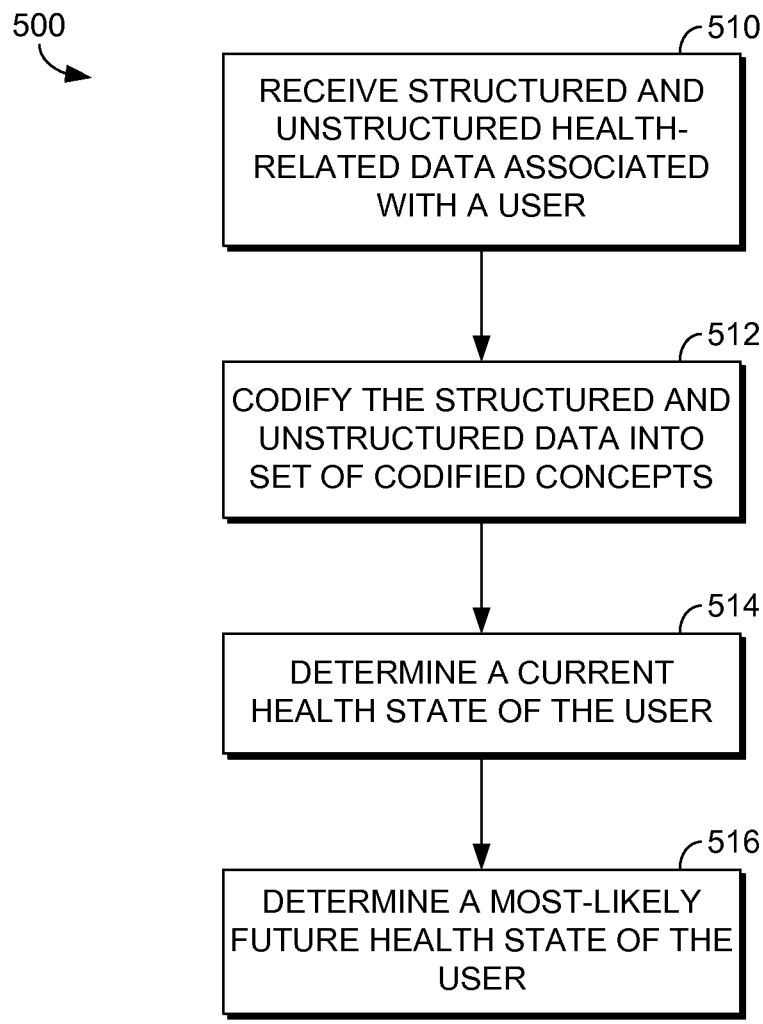
FIG. 5 is a flow diagram that illustrates a method of generating a current and future health state of a user in accordance with an embodiment of the present invention.
Figure 6:
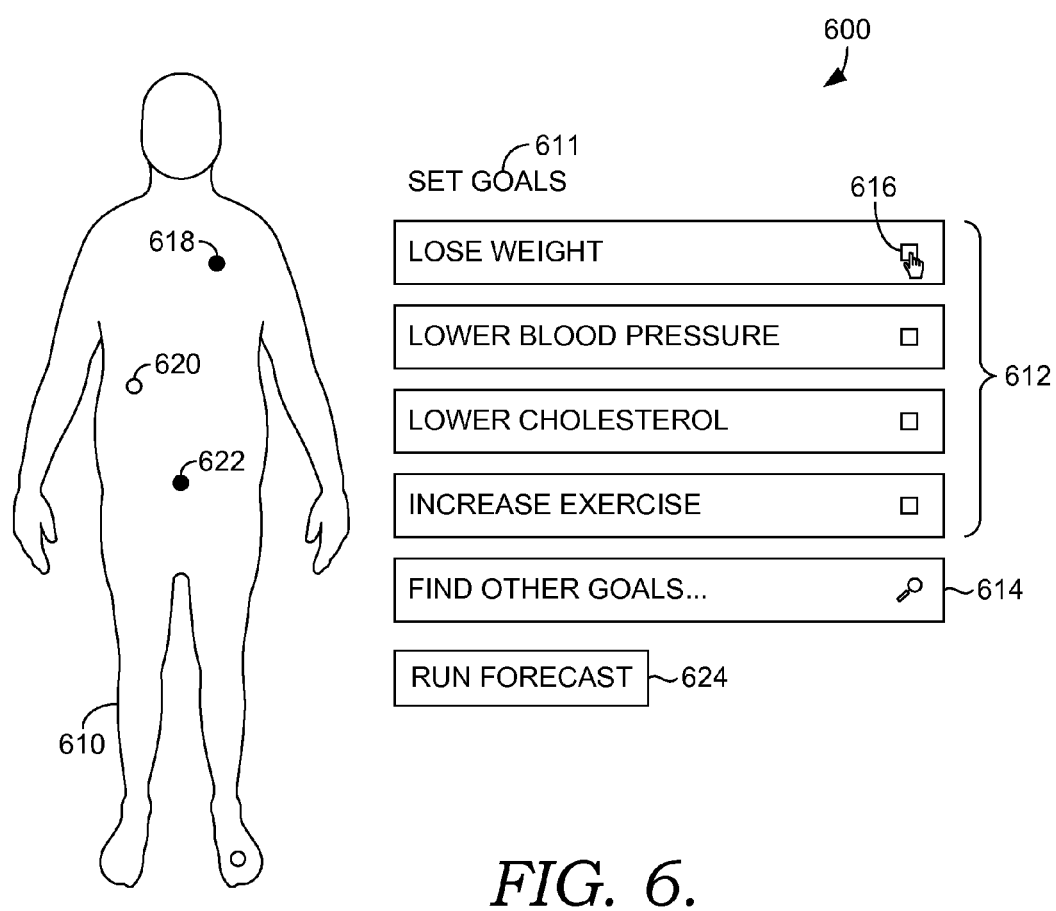
FIG. 6 depicts an exemplary graphical user interface for displaying a body-image representation of a user at a current period of time and goals for achieving an ideal future health state in accordance with an embodiment of the present invention.

Turning now to FIG. 5, an illustrative flow diagram is depicted of a method 500 of generating a current health state of a user and a most-likely future health state of the user. At a step 510, structured and unstructured health-related data associated with a user is received. The data may be received from a data store such as the data store 212 of FIG. 2. The data may also be received via inputs from a healthcare consumer and/or a clinician. The health-related data may comprise data from personal health assessments, biometric screenings, health-related insurance claims, an electronic medical record associated with a user, a clinical care visit, or any combination of the above. Structured data includes data from, for example, health-related insurance claims (structured using ICD-9 codes) while unstructured data may include, for example, radiographs, textual notes from a clinician, and the like.

The data may relate to all aspects of a user's health and may encompass varying time periods. For instance, the data may indicate whether the user is physically active or sedentary, what type of medical conditions the user is suffering from, has suffered from, or is at risk of contracting, what the user's typical diet is, what type of medications the user is currently taking or has taken in the past, previous or current occupational exposures, and the like.

At a step 512, the structured and unstructured data is codified into a set of concepts of standard nomenclature using, for example, SNOMED or LOINC nomenclatures. The purpose of this is to reduce the potentially vast number of health-related variables into a more discrete set of data points. Further, codifying the data facilitates faster processing by a computation component such as the computation component 220 of FIG. 2.

At a step 514, a current health state of the user is determined using PCA. As outlined above, the set of discrete concepts is further reduced to a finite set of factors, and a score is determined for each factor. The score is a number between 0 and 100 and indicates where the user stands in relation to members of the population-at-large with respect to any one factor. In one aspect, the members of the population-at-large are those who share similar demographic traits with the user. An overall health score may be generated as well as any number of sub-health scores. Sub-health scores may correspond to, for example, cardiovascular health, acute injury health, chronic disease health, mental health, female health, diabetic health, and the like.

At a step 516, a most-likely future health state of the user is determined by applying regression analysis in combination with optimal stopping to the set of discrete concepts. The most-likely future health state represents the current trajectory of the user based on the user's current health state and past behaviors. PCA can be used to generate health scores associated with the most-likely future health state.

Turning now to FIGS. 6-10, a progression over time of an exemplary graphical user interface (GUI) 600 is depicted illustrating various graphical representations of health state models. For simplification purposes, similar elements retain the same numbering in the different figures, and new elements are numbered according to the figure on which they are represented. With respect to FIG. 6, the GUI 600 depicts a body-image representation 610 of a current health state of a user as well as a set of goals 611. The body-image representation 610 and the set of goals 611 may be rendered by a rendering component such as the rendering component 222 of FIG. 2. As mentioned, the body-image representation 610 may be customized by the user with respect to gender, body habitus, skin color, hair color, and the like.

The overall visual appearance of the body-image representation 610 provides important information to the user regarding the user's current health state. The overall visual appearance includes a general shape of the body-image representation 610 (thin versus overweight), and/or a colored outline or halo that may indicate certain systemic or multi-organ-system disease conditions. The body-image representation 610 is selectable. For instance, the user may hover over or select the body-image representation 610 to initiate a display screen (not shown) that displays an overall health score and different sub-health scores. The display screen may also include input fields for inputting health scores (or values) that the user would like to achieve.

The body-image representation 610 also provides information to the user by utilizing visual indicators 618, 620, and 622 to indicate areas of concern; the visual indicators 618, 620, and 622 are displayed over an anatomical position that corresponds to an affected organ and/or system. The visual indicators 618, 620, and 622 may comprise dots, stylized versions of the affected organ and/or system, or anatomically correct representations of affected organs and/or systems. Further, the visual indicators 618, 620, and 622 may be color-coded or shaded to indicate a status of the affected organ and/or system. Various colors or shadings may be used to indicate, for example, a "critical" status, a "currently managing" status, a "needs attention" status, an "at risk" status, and a "stable" status.

The visual indicators 618, 620, and 622 are selectable. Upon selection by the user, a detail screen may appear (not shown) that provides more detailed information regarding the selected visual indicator. Information displayed on the detail screen may include a name associated with the visual indicators 618, 620, and 622 (for example, "Type 2 Diabetes"), a status, a health score associated with the visual indicator, when the user was last seen by a clinician, and values associated with the visual indicators 618, 620, and 622. The detail screen may also include input fields for inputting different health scores (or values) that the user would like to achieve with respect to a particular visual indicator. In one aspect, the detail screen may display images of the affected organ and/or system. For example, if the user is suffering from cirrhosis of the liver, the detail screen may display an image of a cirrhotic liver. Further, the detail screen may display an image of the affected organ and/or system at a future time period, or the detail screen may display an image of an organ and/or system of members of the population-at-large that share similar demographic traits as the user. Any and all such variations are within the scope of embodiments of the present invention.

The GUI 600 further includes the goal section 611. The goal section 611 displays any number of selectable goals 612 that are determined based on the ideal future health state the user would like to achieve. For instance, the visual indicator 618 on the body image representation 610 indicates that the user is suffering from some degree of cardiovascular disease (visual indicator 618) that puts the user at the $60^{th}$ percentile with respect to cardiovascular health, and the visual indicator 622 indicates that the user has an increased waist circumference that puts the user at the $65^{th}$ percentile with respect to waist circumference. Additionally, the user's overall health score puts the user at the $55^{th}$ percentile of all healthcare consumers. The user is able to input an ideal future health state based on this information. The user may decide that he or she would like to have an overall health score in the $80^{th}$ percentile, cardiovascular health in the $80^{th}$ percentile and a waist circumference in the $75^{th}$ percentile. The user inputs these parameters into, for example, the inputs fields associated with the body-image representation 610 and the visual indicators 618 and 622, and the selectable goals 612 are generated based on helping the user achieve the selected parameters. The goal section 611 further includes a "Find Other Goals" option 614 that enables the user to search for and select other goals that may be appropriate in helping the user reach the user's ideal future self.

The user is able to select one or more goals that the user is able and willing to carry out. In this example, the user selects the goal "Lose Weight" 616 by checking a box associated with the goal 616. The user can then select a "Run Forecast" option 624 to trigger the generation and display of recommendations geared toward helping the user lose weight.

Figure 7:
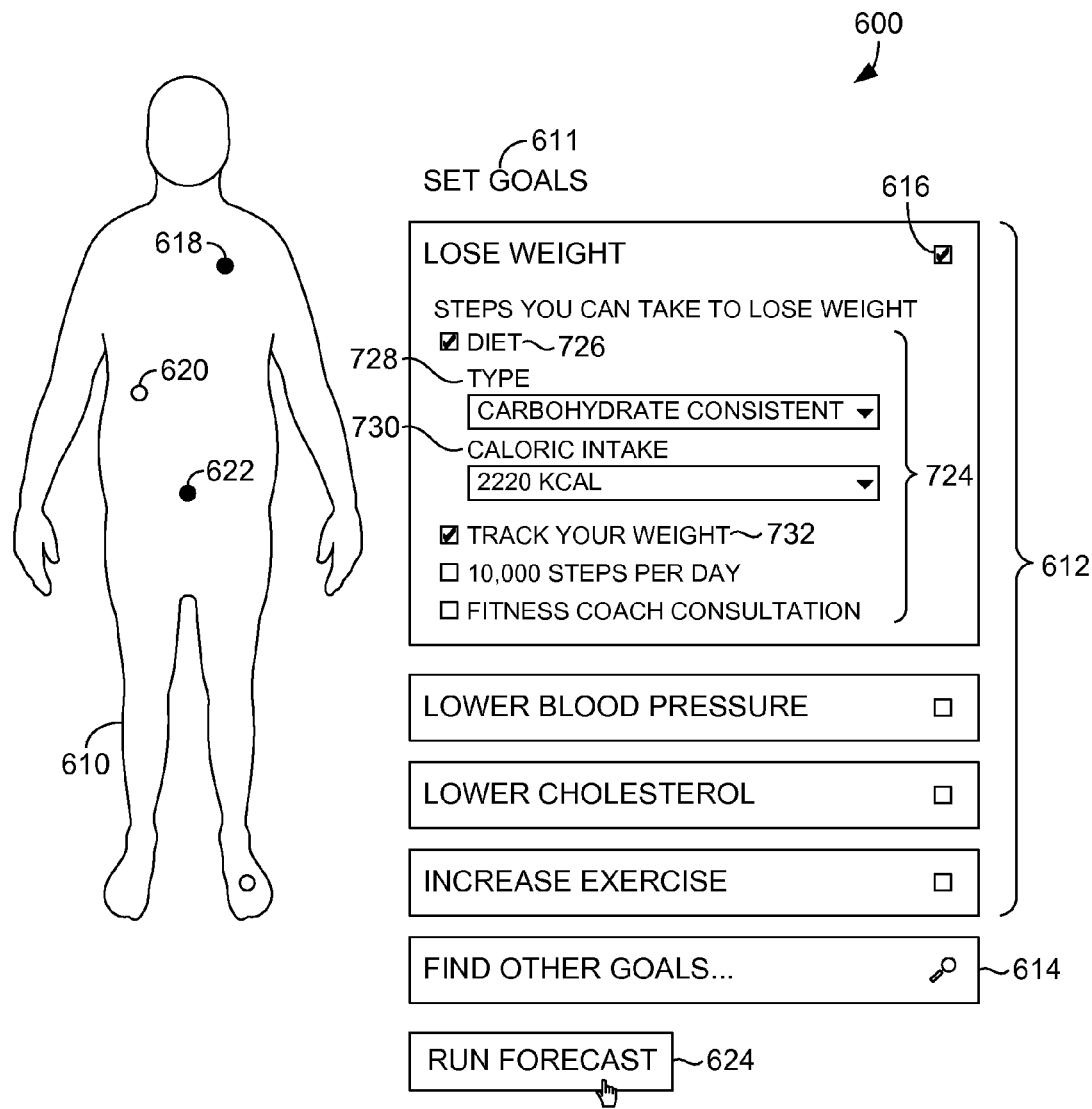
FIG. 7 depicts the exemplary graphical user interface of FIG. 6 illustrating recommendations displayed in response to a user-selection of at least one goal in accordance with an embodiment of the present invention.

Turning now to FIG. 7, the exemplary GUI 600 is displaying recommendations 724 generated in response to the user selecting the "Lose Weight" goal 616. The recommendations 724 may be general recommendations suitable for any healthcare consumer, or the recommendations 724 may be customized based on, for example, demographic features associated with the user, or characteristics that distinguish the user from other healthcare consumers. The characteristics may include disease conditions, genetic characteristics as shown by genetics testing, lifestyle patterns, characteristics revealed by testing, and the like. For instance, medical testing may show that the user would most effectively lose weight utilizing an Atkins-type diet in combination with heavy exercise. In this case, the recommendations 724 would include these parameters.

The user is able to select recommendations from the set of recommendations 724 that the user is able and willing to follow. With respect to FIG. 7, the user has selected "Diet" 726 and "Track Your Weight" 732 but has opted not to include an exercise program or a fitness coach consultation. Upon the user selecting the diet recommendation 726, additional options are presented to the user; these options include type of diet 728 and caloric intake 730. As seen, these options are associated with a drop down list that allows further customization by the user. The user can then select the "Run Forecast" option 624 to trigger the generation and display of graphical representations corresponding to, for example, a most-likely future health state and the user's ideal future health state.

Figure 8:
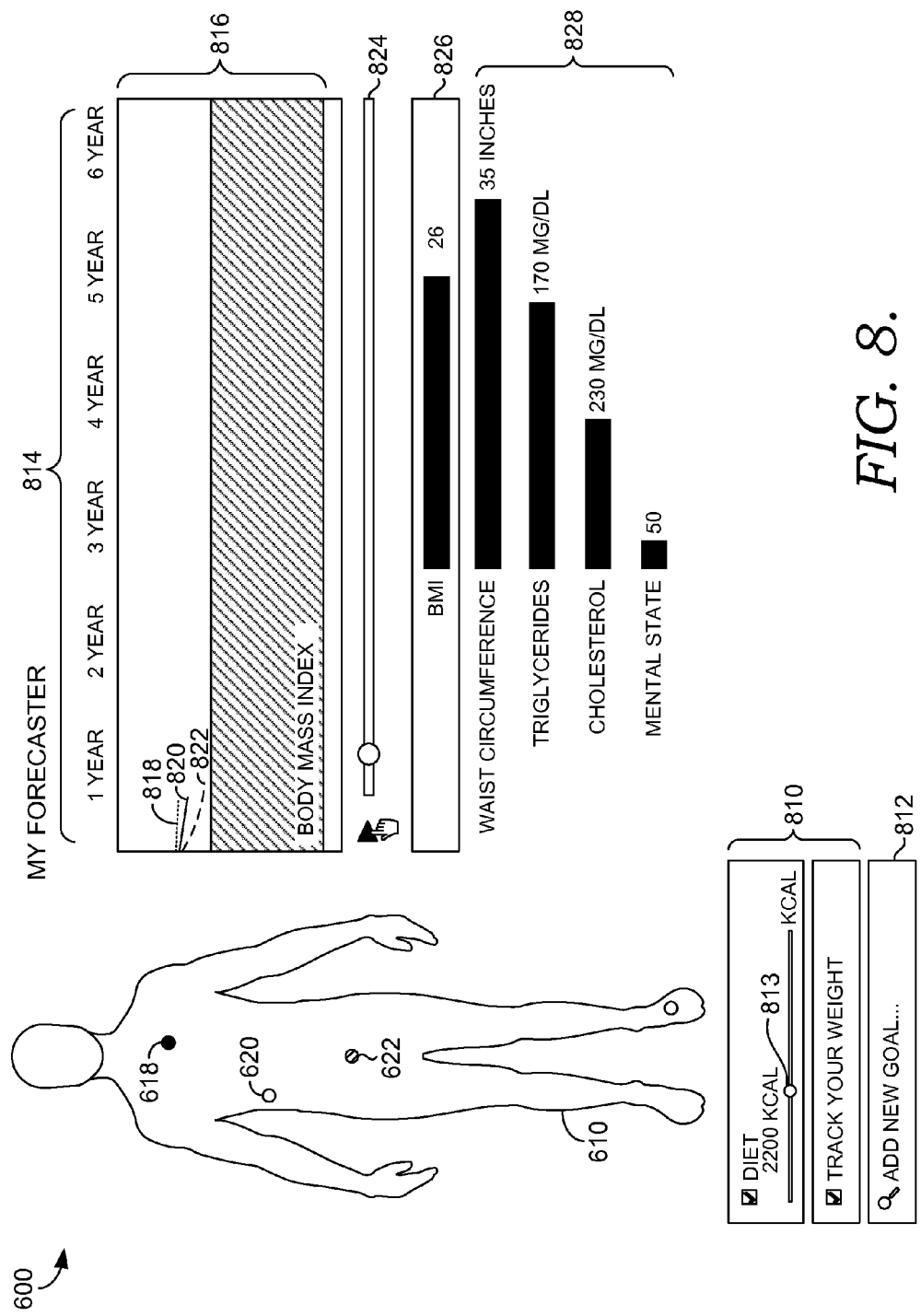
FIG. 8 depicts the exemplary graphical user interface of FIG. 7 illustrating a graphical representation of the user-selected goal over a future period of time displayed in response to a user-selection of a recommendation in accordance with an embodiment of the present invention.

Turning now to FIG. 8, the exemplary GUI 600 is configured to display an interactive time line 814 that depicts future health states associated with the user, a number of health-related variables 826 and 828, the body-image representation 610, and a display of selected recommendations 810. The variables 826 and 828 are the variables determined by a computation component (such as the computation component 220 of FIG. 2) to be associated with the "Lose Weight" goal 616. Referring back to the discussion of PCA above, the "Lose Weight" goal 616 is analogous to a factor, and the variables 826 and 828 are the variables that load on this factor. Each of the variables 826 and 828 is associated with a value and a bar graph corresponding to the value. The values (and the length of the bar graph) associated with the variables 826 and 828 change depending on different selections by the user. For example, the variables 826 and 828 may change in response to the selection of a time period on the timeline 814, or in response to a modification of a recommendation. The user is able to select one or more variables to be displayed on the interactive timeline 814 (in this example, the user has selected the body mass index (BMI) variable 826 to be displayed on the timeline 814).

The interactive timeline 814 displays the selected variable(s) over a future time span. The user is able to select the time span using a control 824 (in this case, the user has selected "1 Year"). The interactive timeline 814 may display the time periods along the top portion of the timeline 814, and values 816 associated with the variable(s) may be displayed along the side(s) of the timeline 814, although other arrangements are contemplated. In one aspect, instead of displaying the values 816 along the side(s) of the timeline 814, percentile ranks may be displayed that enable the user to compare the user's progress or trajectory with other healthcare consumers. One timeline may display multiple variables. Alternatively, multiple timelines may be utilized with each timeline displaying a selected variable. All such examples are within the scope of the invention.

The shaded portion of the timeline 814 indicates a normal value range of the displayed variable. With respect to the GUI 600, a normal range for BMI is displayed. The trajectory path 818 represents the user's trajectory if the user continues with current behaviors and does not adopt any goals or recommendations. The trajectory path 820 represents the user's trajectory based on the selected goals and recommendations. Further, the trajectory path 822 represents an optimal scenario; a scenario where a healthcare consumer has chosen to adopt all or substantially all of the goals and recommendations. Using all three of these trajectory paths on the timeline 814 helps the user to visualize the impact that choices have on future health states.

The body-image representation 610 represents the user at the "1 Year" period based on the user following the selected recommendations. As can be seen, the visual indicator 622 has lightened in appearance indicating that the user's waist circumference is improving. As well, the overall appearance of the body-image representation 610 has altered to visually show the decrease in BMI and waist circumference. As described above, the user can select the visual indicators 618, 620, and 622 as well as the body-image representation 610 to access information regarding the impact the recommendations have had on health scores.

FIG. 8 also includes the display of selected recommendations 810 along with an option 812 to search for and add additional goals. The display of selected recommendations 810 includes a selectable slider bar 813 that enables the user to dynamically adjust the selected recommendations. In this case, the user can choose to increase or decrease the caloric intake. Any changes made using the slider bar 813 would be represented on the timeline 814, the body-image representation 610, and the variables 826 and 828.

Figure 9:
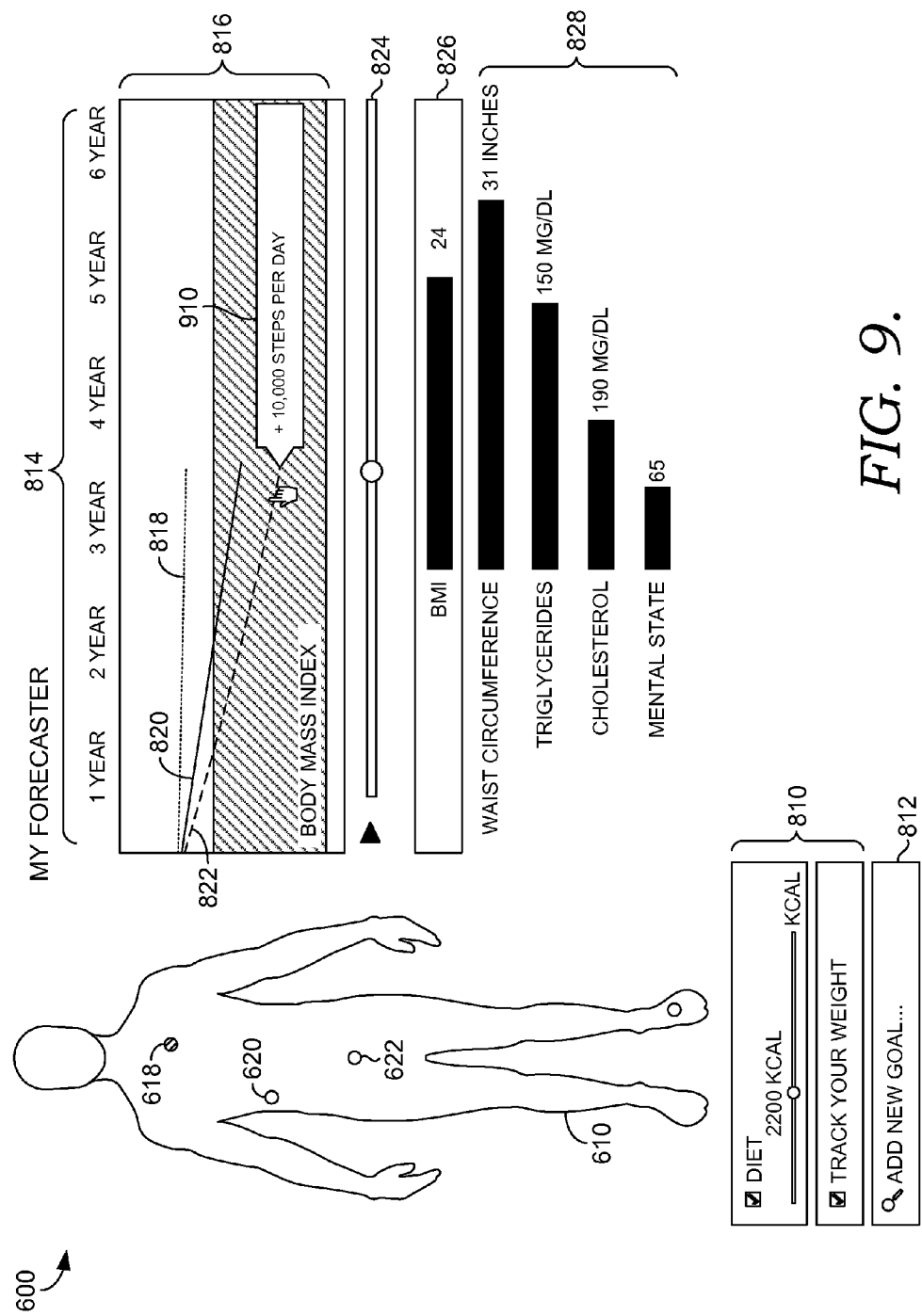
FIG. 9 depicts the exemplary graphical user interface of FIG. 8 illustrating the graphical representation of the user-selected goal over a different future time period and an additional recommendation for achieving the ideal future health state in accordance with an embodiment of the present invention.

Turning now to FIG. 9, the exemplary GUI 600 is depicted at still a later point in time. As can be seen, the user has set the time period to approximately three years using the control 824. The user is able to visually compare the trajectory paths 818, 820, and 822 to see what impact the selected recommendations 810 would have on the BMI variable 826 over a three year time period. Further, the user is able to select the trajectory path 822 to see what additional recommendations 910 healthcare consumers follow who fall along this trajectory. Thus, in this case, healthcare consumers who follow the trajectory path 822 walk and/or run 10,000 steps per day. The user can choose to add this recommendation to the user's own set of recommendations 810. This is depicted in FIG. 10.

FIG. 9 also depicts the body-image representation 610 three years in the future; the body-image representations 610 corresponds to the trajectory path 820. The visual indicator 622 now comprises an open circle indicating that the waist circumference is stable and no longer an area of concern. Additionally, the visual indicator 618 is shaded lighter indicating that cardiovascular health is improving but still needs attention. The variables 826 and 828 also flex to reflect responses to the selected recommendations 810. As can be seen, many of the values associated with the variables 826 and 828 have improved; the bar graphs reflect these new values. Additionally, the slimmer, overall appearance of the body-image representation 610 reflects the impact of the selected recommendations 810.

Figure 10:
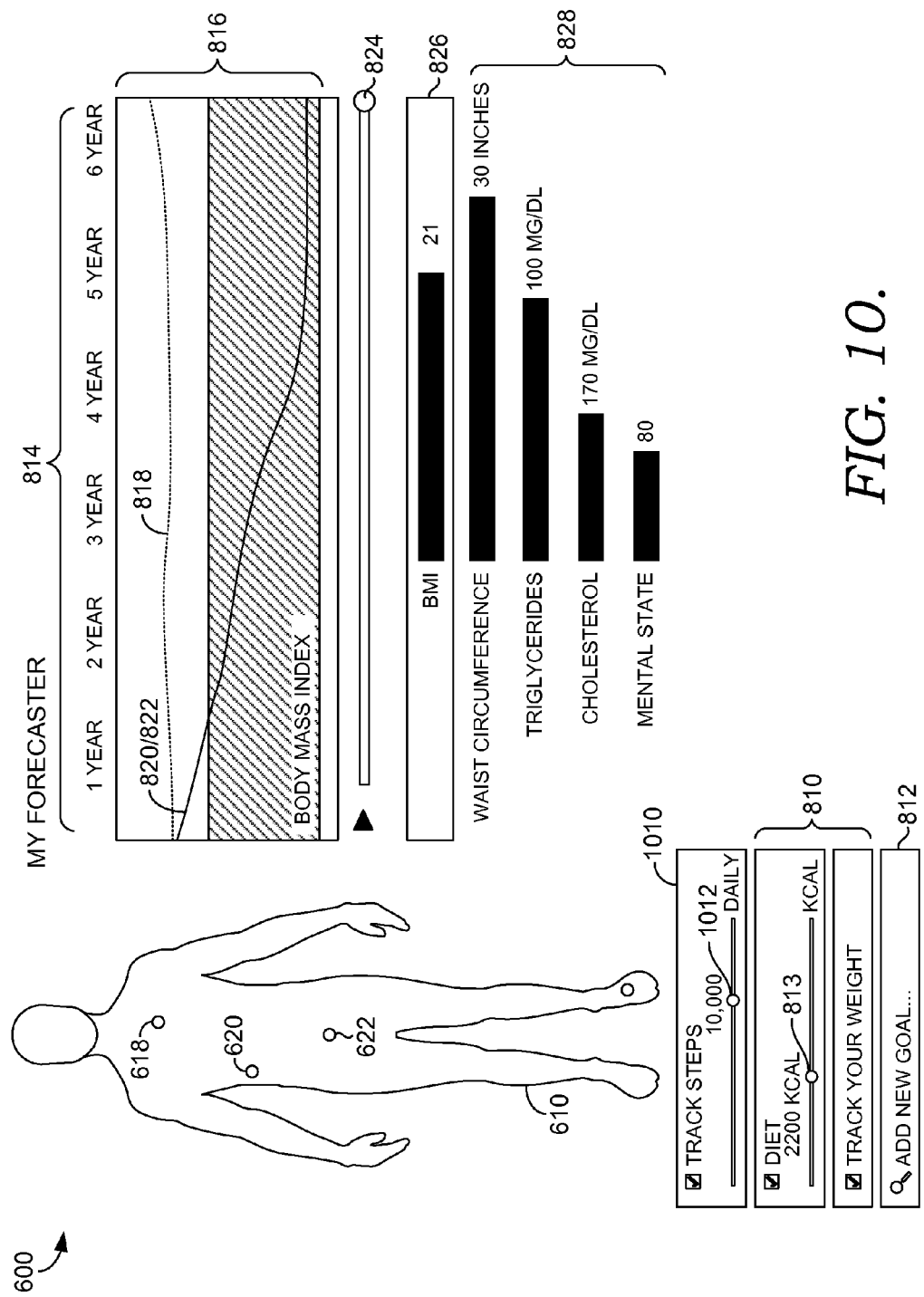
FIG. 10 depicts the exemplary graphical user interface of FIG. 9 illustrating the graphical representation of the user-selected goal over an additional future time period.

Turning to FIG. 10, the exemplary GUI 600 is depicted at a still later point in time. The recommendation 910 ("10,000 Steps Per Day") on FIG. 9 was added by the user to the display of selected recommendations 810. This is shown by element 1010 ("Track Steps"). The user can adjust the number of steps per day using the control 1012. The timeline 814 is now set for six years in the future and has flexed in appearance to demonstrate the influence of adding 10,000 steps per day to the user's selected recommendations 810. The user's ideal trajectory 820 has now merged with the optimal trajectory 822. Again, the trajectory path 818 demonstrates the user's future path if no recommendations are followed. The variables 826 and 828 have also changed in response to the new time period and the addition of exercise.

The body-image representation 610 continues to evolve to reflect the influence of the selected recommendations. For instance, the visual indicator 618 now appears as an open circle indicating that cardiovascular health is no longer an area of concern. The overall appearance of the body-image representation 610 shows a slimmer, more fit user.

In conclusion, the health forecaster is a powerful tool for predicting future health states based on current health states and for providing visual encouragement to healthcare consumers to make needed changes to their health habits to ensure a healthier future.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. One or more computer-readable storage media having embodied thereon computer executable instructions that, when executed by a server, perform a method of using health-related variables associated with a subject having a health condition to generate current and future health states of the subject, the method comprising:
   receiving structured and unstructured health-related data associated with the subject having the health condition, the structured and unstructured health-related data comprising data over a past period of time up to a current period of time, the structured and unstructured health-related data comprising data received from at least one of personal health risk assessments, biometric screenings, and health-related insurance claims associated with the subject;
   codifying the structured and unstructured health-related data into a set of codified concepts of standard nomenclature;
   utilizing the set of codified concepts, generating:
      at least a first health score that represents the current health state of the subject, wherein the at least the first health score comprises a percentile comparison of the subject's current health state to health states of people who share one or more demographic traits with the subject,
      at least a second health score that represents the future health state of the subject, wherein the at least the second health score comprises a percentile comparison of the subject's future health state to health states of the people who share one or more demographic traits with the subject, and wherein the at least the second health score is determined by applying regression analysis to the set of codified concepts of standard nomenclature;
   generating a first graphical representation of the current health state of the subject and generating a second graphical representation of the future health state of the subject, wherein the first graphical representation comprises a first anatomically correct body-image representation of the subject and the second graphical representation comprises a second anatomically correct body-image representation of the subject, wherein at least the first anatomically correct body-image representation further comprises one or more automatically updateable visual indicators indicating areas of concern for the subject based on the current health state of the subject and the future health state of the subject, and when there are multiple body systems affected by a particular condition, outlining at least the first anatomically correct body-image representation with a particular type of line representing the particular condition; and
   rendering the first and second graphical representations on a graphical user interface (GUI).

2. The media of claim 1, wherein the structured and unstructured health-related data are codified using at least one of Systemized Nomenclature of Medicine (SNOMED) or Logical Observation Identifiers Names and Codes (LOINC).

3. The media of claim 1, wherein the at least the first and second health scores are generated using Principal Component Analysis (PCA).

4. The media of claim 1, further comprising:
   receiving one or more subject selections associated with the first graphical representation;
   determining goals and recommendations based on the current health state of the subject and the one or more subject selections, wherein the goals and recommendations are related to the subject achieving an improved future health state as compared to the current health state;
   presenting the goals and recommendations on the GUI;
   receiving one or more subject selections of the goals and recommendations;
   generating a third graphical representation of the improved future health state based on the one or more subject selections of the goals and recommendations; and
   rendering the third graphical representation of the improved future health state on the GUI.

5. The media of claim 1, wherein the particular type of line representing the particular condition comprises a colored halo, wherein a color of the colored halo is predetermined according to a color code.

* * * * *